April 4, 1972 H. C. SWIM ET AL Plant Pat. 3,098
ROSE PLANT
Filed April 6, 1970
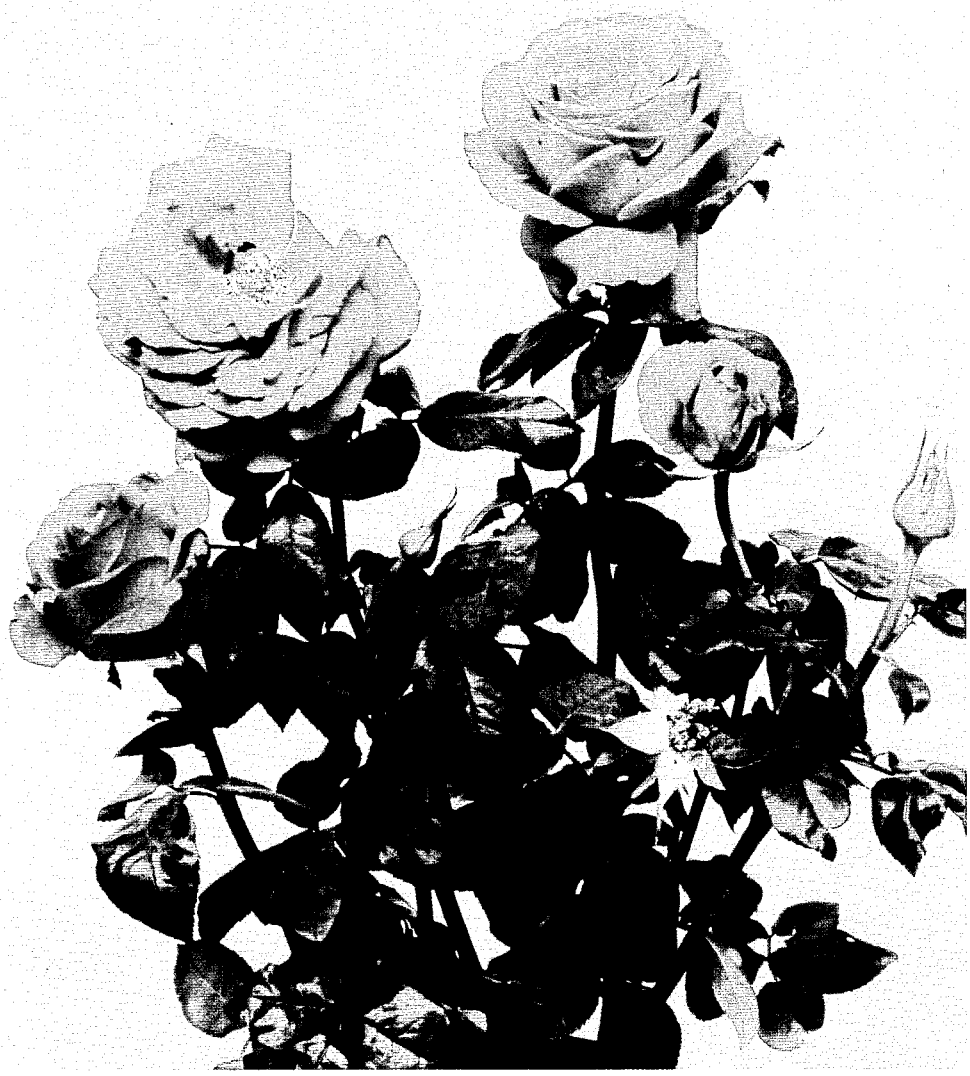
Inventors.
H. C. Swim
O. L. Weeks
By: Robbins & Robb
Attorneys.

United States Patent Office

Plant Pat. 3,098
Patented Apr. 4, 1972

3,098
ROSE PLANT

Herbert C. Swim and O. L. Weeks, Ontario, Calif., assignors to O. L. Weeks, doing business as Weeks Wholesale Rose Grower, Ontario, Calif.

Filed Apr. 6, 1970, Ser. No. 26,176
Int. Cl. A01h 5/00
U.S. Cl. Plt.—20 1 Claim

The present invention relates to a new and distinct variety of rose plant of the hybrid tea class, which was originated by us by crossing an unnamed and unpatented seedling derived from a cross of ["First Love" (Plant Patent No. 921)×"Queen Elizabeth" (Plant Patent No. 1,259)]×"Chrysler Imperial" (Plant Patent No. 1,167), with the rose variety known as "Night 'N' Day" (Plant Patent No. 2,655), said unnamed seedling being the pollen parent and "Night 'N' Day" being the seed parent.

As the result of this breeding, we have produced a new and improved rose variety which is distinguished from its parents, as well as from all other rose varieties of which we are aware, as evidenced by the following unique combination of characteristics which are outstanding in the new variety:

(1) An unusually tall and vigorous plant habit, but with a fullness which adds to the overall effect of being complete with ample foliage of good quality;
(2) A habit of producing flowers in a true hybrid tea manner and borne almost without exception on long, single stems which are of heavy caliper and strong;
(3) Consistently large flowers having above average petal substance which permits each flower to retain a classic high-centered fullness both on the plant and as cut flowers for long periods of time;
(4) A distinctive and attractive deep reddish purple overall flower color, but having a more vivid, velvety red shading on the inside of the petals; and
(5) A complete absence of thorns on all new growth, with a consequent easier handling ability as cut flowers.

In comparison with its pollen parent, the plant of our new rose variety is more vigorous and of more compact and symmetrical form; its flowers are borne almost entirely on long and strong single stems, whereas those of this parent are often borne in candelabra clusters on stems of less length and strength; and the flowers of the new variety are of larger size, considerably more uniform and of classic petal formation, and have greater substance and longevity than the flowers of the pollen parent.

As compared with its seed parent "Night 'N' Day," the new variety is a free and profuse bloomer and bears flowers in great abundance throughout the blooming season, contrary to the sparse and intermittent blooming habit of this parent; its flowers are smaller in size and are of compact, classic, high-centered conformation in contrast with the unevenly opening habit in an irregular petal pattern typical of the parent; the flower color of the new variety is quite uniform and essentially in the reddish purple range, whereas the flowers of this seed parent have little or no purple pigment and the center petals are noticeably brighter red; and the new variety is free of thorns on all cutting stems contrary to the thorny stems of "Night 'N' Day."

Asexual reproduction of our new variety by budding, as performed at Chino, Calif., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Md., except where general color terms of ordinary dictionary significance are obvious:

Type: Hardy; tall; bush; outdoor; seedling; for cut flowers and for garden decoration.
Class: Hybrid tea.
Breeding: Seedling.
*Seed parent.*—"Night 'N' Day."
*Pollen parent.*—An unnamed seedling of "First Love" ×"Queen Elizabeth"×"Chrysler Imperial."
Propagation: Holds its distinguishing characteristics through succeeding propagations by budding.

Flowers

Locality where grown and observed: Chino, Calif.
Flowers borne: Singly; on long and strong stems.
Quantity of bloom: Free, both outdoors and in greenhouse.
Continuity: From intermittent to continuous.
Fragrance: Slight, but becoming more noticeable as flower opens. Nature—Tea.
Bud:
*Peduncle.*—From medium length to long; heavy caliper; erect; stiff; almost smooth; very few prickles. Color—Medium grey-green.
*Before calyx breaks.*—Size—From medium to small. Form—From short to medium length; from pointed to ovoid; with foliaceous appendages on the surface of the bud; with foliaceous parts extending beyond the tip of the bud equal to ¼ of its length.
*As calyx breaks.*—Color—Somewhat darker than medium to Dark Red, Hue 10 RP 4/12.
*As first petal opens.*—Size—From medium to large. Form—From pointed to ovoid. Color—Outside—From Deep Purplish Red, Hue 10 RP 3/10 to Strong Purplish Red, Hue 10 RP 4/12. Inside—From Dark Red, Hue 2.5 R 3/7 to Strong Purplish Red, Hue 10 RP 3/10, but slightly redder.
*Opening.*—Opens up well.
Bloom:
*Size (when fully open).*—From medium to large; from 3½ inches to 5 inches.
*Petalage.*—Double; many petals, usually with no stamens showing; from 38 to 42 petals; arranged regularly.
*Form.*—Full and high-centered and remaining high-centered.
Petals:
*Texture.*—Thick; leathery.
*Appearance.*—Inside—Shiny and velvety. Outside—Shiny.
*Shape.*—Outside—Broadly round; scalloped; entire; with apex flat. Intermediate—Scalloped; with apex flat. Inside—Broadly round; entire; with apex flat.

This description of a newly opened flower was made from a rose grown outdoors during the month of October at Ontario, Calif.

Color:
*Outer petal.*—Outside surface—Deep Purplish Red, Hue 10 RP 3/10, with base Brilliant Yellow Green, Hue 2.5 GY 9/8. Inside surface—Strong Purplish Red, Hue 10 RP 4/12, with base Brilliant Yellow Green, Hue 2.5 GY 9/8.
*Intermediate petal.*—Outside surface—From Deep Purplish Red, Hue 10 RP 3/10 to Strong Purplish Red, Hue 10 RP 4/12, with base Brilliant Yellow Green, Hue 2.5 GY 9/8. Inside surface—Strong Purplish Red, Hue 10 RP 4/12, with tip of base Brilliant Yellow Green, Hue 2.5 GY 9/8.

*Inner petal.*—Outside surface—Deep Purplish Red, Hue 10 RP 3/10, except Strong Purplish Red, Hue 10 RP 4/12 at tip and Brilliant Yellow Green, Hue 2.5 GY 9/8 at base. Inside surface—From Dark Red, Hue 2.5 R 3/7 to slightly redder than Moderate Red, Hue, 2.5 R 4/10 at tip, with Brilliant Yellow Green, Hue 2.5 GY 9/8 at extreme base.

This description was made from a rose that was open for three days outdoors during the month of October at Ontario, Calif.

Color:

*Outer petal.*—Outside surface—Between Strong Purplish Red, Hue 7.5 RP 4/11 and Strong Purplish Red, Hue 10 RP 3/10, with Brilliant Yellow Green, Hue 2.5 GY 9/8 at base. Inside surface—Between Strong Purplish Red, Hue 7.5 RP 4/11 and slightly redder than Strong Purplish Red, Hue 10 RP 4/12, with Brilliant Yellow Green, Hue 2.5 GY 9/8 at base.

*Inner petal.*—Outside surface—Near Deep Purplish Red, Hue 10 RP 4/12, with Brilliant Yellow Green, Hue 2.5 GY 9/8 at base. Inside surface—From Moderate Red, Hue 2.5 R 4/10 to slightly redder than Strong Purplish Red, Hue 10 RP 3/10, with Brilliant Yellow Green, Hue 2.5 GY 9/8 at base.

General color effect:

*Newly opened flower.*—From Strong Purplish Red to Deep Red.

*3-days open.*—From Purplish Red to Dark Red, with inside of petals being a more vivid velvety red.

Behavior—Drop off cleanly.

Flower longevity:

*On bush in garden.*—5 days or more all season.

*Cut roses grown outdoors and kept at living room temperatures.*—6 days or more during any month.

Reproductive organs

Stamens: Many; arranged irregularly about pistils; tucked in calyx.

Filaments: Medium length; many with anthers. Color—Pink.

Anthers: Medium size; all open at once. Color: Yellow.

Pollen: Abundant. Color—Yellow.

Pistils: Many.

Styles: Uneven length, but mostly long; medium caliper; bunched.

Stigma: Color—White.

Ovaries: All protruding from calyx.

Hips: None observed.

Sepals: Permanent; recurved.

Seeds: None observed.

Plant

Foliage:

*Leaves.*—Compound of 5–7 leaflets; normal abundance; medium size; heavy; semi-glossy.

*Leaflets.*—Shape—Ovate. Apex—Acute. Base—Obtuse. Margin—Simply serrate.

*Color.*—Mature—Upper surface—Moderately dark green. Under surface—Moderately light grey-green. Young—Upper surface—Moderately Green, with some reddish purple overlay on veins. Under surface—Moderately light grey-green.

*Rachis (the supporting stem of the compound leaf).*—Heavy. Upper side—Smooth. Under side—Moderately smooth.

*Stipules.*—Moderately short; medium width; with medium length points turning out at an angle of more than 45°.

*Disease resistance.*—Above average resistance to powdery mildew, as determined by comparison with other rose varieties grown under comparable conditions at Ontario, Calif.

Growth:

*Habit.*—Tall; upright; much-branched.

*Growth.*—Very vigorous.

*Canes.*—Moderately heavy.

*Main stems.*—Color—Dull green. Large prickles—From none to few; medium length; straight; with long, narrow base. Color—From green to yellowish green. Small prickles—None. Hairs—None.

*Branches.*—Color—From bright to dull yellowish green. Large prickles—None. Small prickles—None. Hairs—None.

*New shoots.*—Color—From bright to dull yellowish green, with some purple overlay. Large prickles—None; free of thorns on all cutting stems. Small prickles—None. Hairs—None.

We claim:

1. A new and distinct variety of rose plant of the hybrid tea class, substantially as herein shown and described, characterized particularly as to novelty by the unique combination of an unusually tall and vigorous plant habit, but with a fullness which adds to the overall effect of being complete with ample foliage of good quality, a habit of producing flowers in a true hybrid tea manner and borne almost without exception on long, single stems which are of heavy caliper and strong, consistently large flowers having above average petal substance which permits each flower to retain a classic high-centered fullness both on the plant and as cut flowers for long periods of time, a distinctive and attractive deep reddish purple overall flower color, but having a more vivid, velvety red shading on the inside of the petals, and a complete absence of thorns on all new growth, with a consequent easier handling ability as cut flowers.

No references cited.

ROBERT E. BAGWILL